(12) United States Patent
Togashi et al.

(10) Patent No.: US 9,415,155 B2
(45) Date of Patent: Aug. 16, 2016

(54) INJECTOR PISTON NEST

(75) Inventors: Hiroshi Togashi, Tokyo (JP); Jansen Hubert, Stolberg (DE)

(73) Assignees: DAIKYO SEIKO, LTD., Tokyo (JP); WEST PHARMACEUTICAL SERVICES, INC., Lionville, PA (US)

( * ) Notice: Subject to any disclaimer, the term of this patent is extended or adjusted under 35 U.S.C. 154(b) by 1258 days.

(21) Appl. No.: 12/224,392

(22) PCT Filed: Feb. 28, 2006

(86) PCT No.: PCT/JP2006/304226
§ 371 (c)(1),
(2), (4) Date: Nov. 18, 2008

(87) PCT Pub. No.: WO2007/099649
PCT Pub. Date: Sep. 7, 2007

(65) Prior Publication Data
US 2009/0095647 A1  Apr. 16, 2009

(51) Int. Cl.
*A61B 19/02* (2006.01)
*A61M 5/00* (2006.01)
*A61M 5/315* (2006.01)

(52) U.S. Cl.
CPC ............... *A61M 5/008* (2013.01); *A61M 5/002* (2013.01); *A61M 2005/31506* (2013.01)

(58) Field of Classification Search
CPC ............... A61M 5/008; A61M 5/002; A61M 2005/31506

USPC ......... 206/439, 363, 366, 370, 563, 443, 446, 206/364, 486, 562, 565
See application file for complete search history.

(56) References Cited

U.S. PATENT DOCUMENTS

| 1,833,461 | A | * | 11/1931 | Grupe | 492/28 |
| 4,913,286 | A | * | 4/1990 | Tate | 206/728 |
| 5,823,363 | A | * | 10/1998 | Cassel | 206/366 |
| 6,164,044 | A | * | 12/2000 | Porfano et al. | 53/471 |
| RE38,312 | E | * | 11/2003 | Gamble | 422/553 |
| 6,719,141 | B2 | * | 4/2004 | Heinz et al. | 206/563 |

FOREIGN PATENT DOCUMENTS

| JP | 2001-327577 | 11/2001 |
| JP | 2002-326126 | 11/2002 |
| JP | 2003-210578 | 7/2003 |
| JP | 2004-513708 | 5/2004 |

* cited by examiner

*Primary Examiner* — Andrew Perreault
(74) *Attorney, Agent, or Firm* — Manabu Kanesaka (57) ABSTRACT

A container for receiving or storing or carrying pistons for injectors, the container having a base plate and hollow cylindrical piston storage parts (the container being hereafter referred to as a piston nest). Each of the hollow cylindrical piston receiving parts is formed either by making it vertically penetrate through the basic plate, with one side of the base plate functioning as one opening end, and project from the other side or by making it vertically penetrate through the base plate and project from both sides of the base plate. Preferably, each piston receiving part has a swelled part where a part of the inner peripheral wall surface of the piston receiving part is swelled inward. The pistons for injectors are received in the piston receiving parts.

6 Claims, 6 Drawing Sheets

Fig. 7

INJECTOR PISTON NEST

BACKGROUND OF THE INVENTION

1. Field of the Invention

This invention relates to a container for housing, storing or transporting an injector piston, which will be hereinafter referred to as a piston nest.

2. Prior Art

Figure 7:
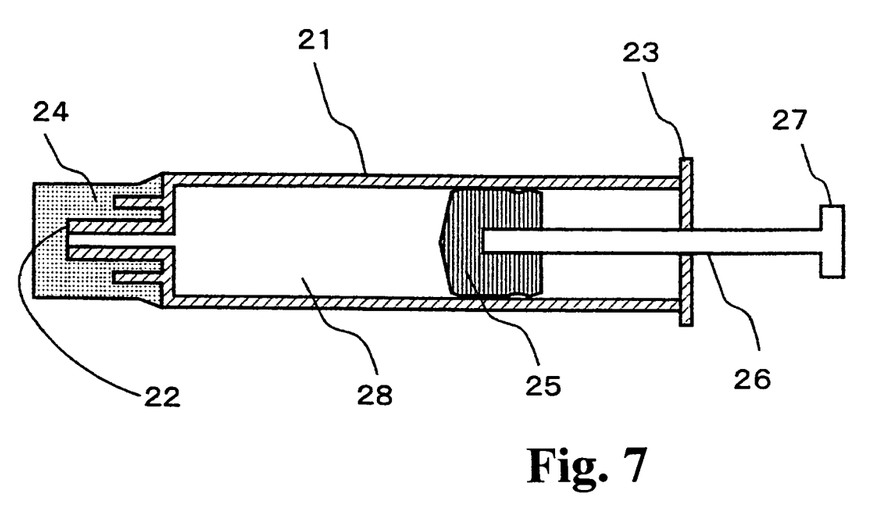
FIG. 7 is a schematic sectional view of a basic injector.

As shown in FIG. 7, an injector basically consists of each component comprising an injection cylinder 21 in which injection liquid 28 is filled, a piston 25 inserted slidably into the injection cylinder 21, a nozzle cap 24 for detachably sealing a tip portion 22 of the injection cylinder 21, and a plunger 26 for pushing the piston 25 so that the injection liquid 28 filled in the injection cylinder 21 is flowed out thereof through the tip portion 22.

Pre-filled syringes are now getting popular and are on the market as syringe products in which injection liquid is filled in advance in an injector comprising above mentioned components in combination. Such pre-filled syringes are usually fabricated on a production line of pharmaceutical companies. The nozzle cap 24 is generally capped on the tip portion 22 of the injection cylinder 21 followed by filling the injection liquid 28 therein, and then the piston 25 is inserted to seal the liquid 28.

In general, these components have been conventionally subjected to a cleaning or sterilizing treatment just before their fabrication on the production line so as to fill the injection liquid.

However, the cleaning or sterilizing treatment of injector components is troublesome to pharmaceutical companies, and this is the reason why they strongly request syringe component manufacturers to deliver cleaned or sterilized products.

In order to respond to such a request, the manufacturers tried to control production environments and qualities and, as to the injection cylinder, developed an injector carrying container disclosed in Japanese Patent A Nos. 2004-513,707 and 2004-513-708, thereby making it possible for the pharmaceutical companies to use injectors by simply subjecting the cylinder as a package to the sterilizing treatment. Further, the nozzle cap 24 and the piston 25 are packed in a packaging bag called as a sterilizing bag, partially made of a material such as TYVEK® which selectively passes ethylene oxide gas and vapor but does not passes fine particles and microorganisms, so that the pharmaceutical companies can use these components as they are by simply sterilizing them similarly as the injection cylinder.

The nozzle cap 24 and the piston 25 are usually packed in the sterilizing bag as a unit of several hundreds to several thousands of the same components, which would result in fine particles or outside flaws thereof caused by their vibration and mutual friction during transportation.

On the other hand, when these components are assembled into the injection cylinder after their unpacking, an aligner is necessary to keep them in the same direction, which would cause not only fall off of workability but contamination of foreign substance. From this point of view, it has been expected to develop a packaging method and a packaging container which does not result in flaws nor contamination of foreign substance during transportation or fabrication of injector components.

SUMMARY OF THE INVENTION

This invention has been completed to improve packaging of injector piston in consideration of the present situation thereof and, accordingly, it is an object of the invention is to provide a piston nest which prevents development of flaws on the piston or contamination of foreign substance therein during packing, packaging, storing and transportation and makes it hygienic and easy to assemble components into an injector.

The inventors have keenly investigated a structure exclusively used for independently housing, storing and transporting plural injector pistons in a container, instead of a conventional manner for randomly bagging, packaging, storing and transporting plural injector pistons (hereinafter sometimes simply referred to as piston(s)).

There have been formed plural housing portions on a base material, where each piston is housed, stored and transported. As a result, it is possible to prevent development of flaws on the piston and contamination of foreign substance and to assemble the piston into an injector without using an aligner. Further, when the present container is used together with a similar container or nest exclusively used for other injector components, there can be simplified to take out pistons and other components from their package and to assemble them into injectors, thereby the object of this invention being achieved.

The object of this invention will be more definitely achieved as in the following:

1. A piston nest for housing injector pistons in a free run situation which comprises a base material and plural cylindrical housing portions for injector pistons, one surface of said base material being opened as open ends while said plural cylindrical housing portions being formed by piercing said base material vertically thereto and protruding to an opposite surface of said material.
2. A piston nest for housing injector pistons in a free run situation which comprises a base material and plural cylindrical housing portions for injector pistons, said plural cylindrical housing portions being formed by piercing said base material vertically thereto and protruding from both surfaces of said base material.
3. A piston nest for housing injector pistons described in the item 1 or 2 above in which expanded portions are formed by expanding an inner wall of said piston housing portions inwardly on an inner peripheral surface thereof
4. A piston nest for housing injector pistons described in the item 3 above in which said expanded portions are formed in the shape of ring on the same inner peripheral surface of said piston housing portions.
5. A piston nest for housing injector pistons described in the item 3 above in which said expanded portions are dotted in the shape of bump on the same inner peripheral surface of said piston housing portions.
6. A piston nest for housing injector pistons described in any item 1 to 5 above in which an inner diameter of said piston housing portions except that of said expanded portions is nearly uniform.
7. A piston nest for housing injector pistons described in any item 1 to 5 above in which an inner diameter of said piston housing portions except that of said expanded portion diminishes from one side of open ends to the other side.
8. A piston nest for housing injector pistons described in the item 6 or 7 above in which an opened diameter of either one side of an open end of said piston housing portions is smaller than an outer diameter of an injector piston.
9. A piston nest for housing injector pistons described in any item 1 to 8 above in which an injection piston is housed in said piston nest for housing injector pistons.
10. A piston nest for housing injector pistons described in the item 9 above in which said injector piston has an indent on a part of its outer peripheral surface in the peripheral direction so that said injector piston is kept in said piston housing portion by junction of said indent with said expanded portion of said piston housing portion.

11. A piston nest for housing injector pistons described in the item 9 or 10 above in which clearance is at least partially left between an outer peripheral surface of said injector piston and an inner peripheral surface except said expanded portion on said piston housing portion.

BRIEF DESCRIPTION OF THE DRAWINGS

FIG. 1 is a perspective view (a), a plan view (b) and a vertical sectional view (c) of an injector piston nest of this invention as an example.

EFFECTS OF THE INVENTION

According to a piston nest of this invention, plural cylindrical piston housing portions are formed on a base material surface to independently house each injector piston, which has already been subjected to a treatment of cleaning or sterilization, thereby inhibiting contamination of foreign substance and development of surficial flaws caused by peripheral friction of pistons in the course of packing, packaging, storage or transportation. Further, fabrication of the piston with other injector components to assemble into an injector can be done hygienically and simply.

The Preferred Embodiments

Referring now to the drawings, this invention will be described in detail in the following.

Figures 1A, 1B, 1C:
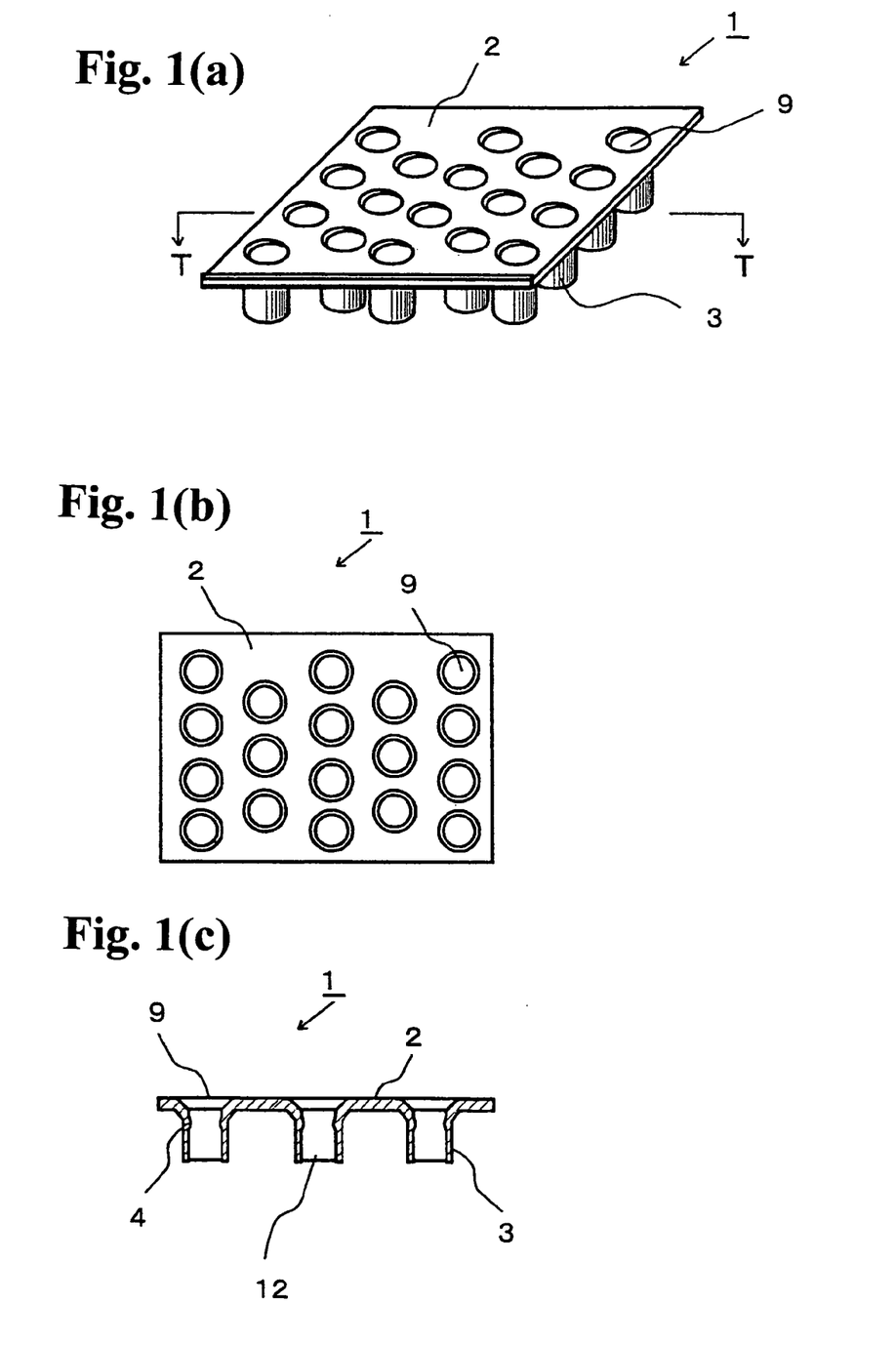
Figure 2A:
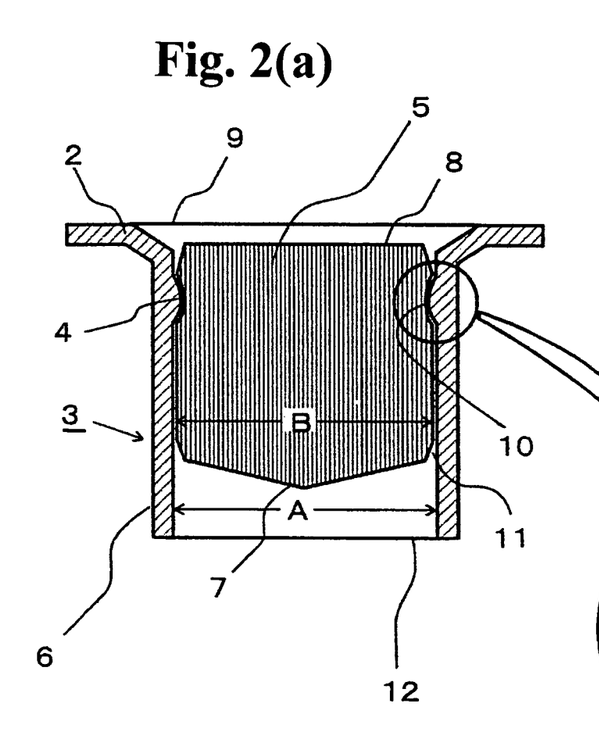
FIG. 2 is a sectional view of an injector piston nest of this invention with a piston housed therein taken from a parallel surface to the axis.
Figure 2B:
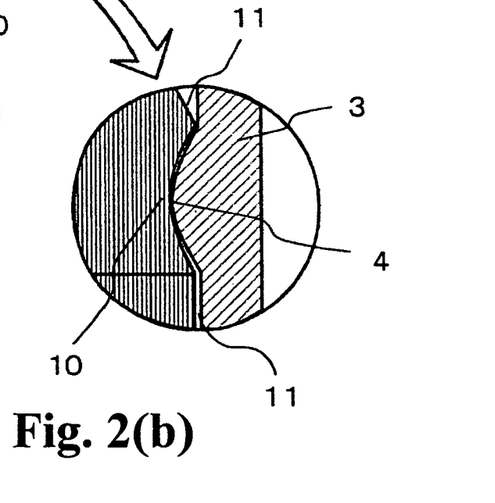
Figure 3:
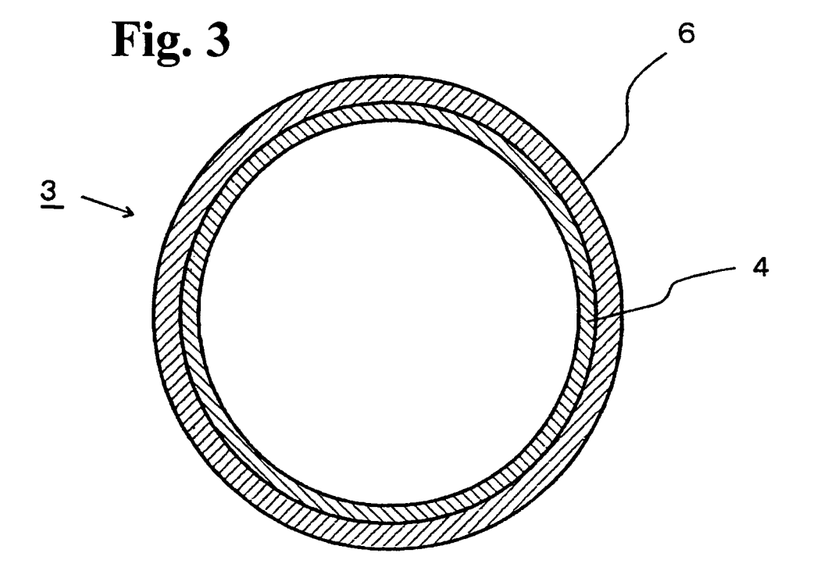
FIG. 3 is a bottom view of an injector piston nest of this invention without a piston taken from a tip 7 side of a piston 5.
Figure 4:
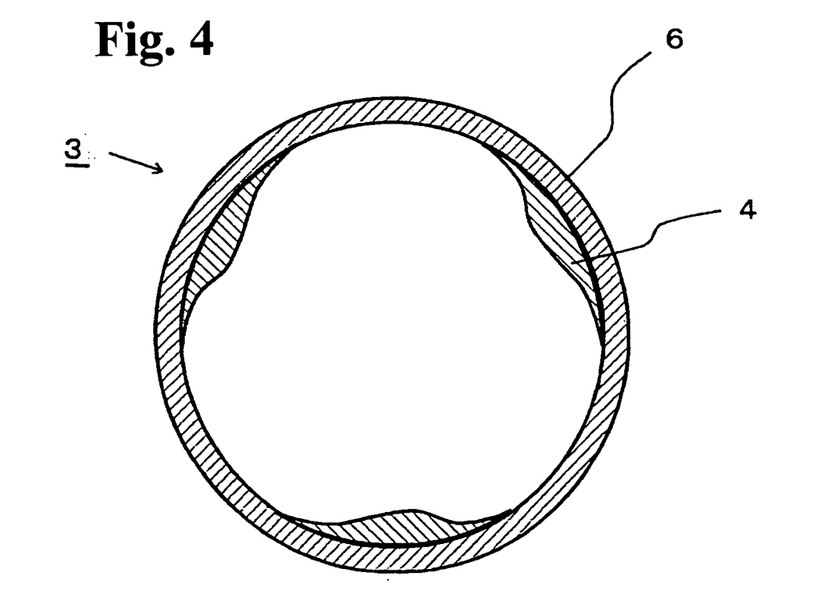
FIG. 4 is a bottom view of another injector piston nest of this invention without a piston taken from a tip 7 side of a piston 5.

FIG. 1 shows an embodiment of the present piston nest, in which (a) and (b) are perspective and plan views and (c) is a sectional view taken on line T-T in Fig. (a). FIG. 2 (*a*) is an axially parallel sectional view of an injector piston nest of this invention with a piston housed therein, while FIG. 2 (*b*) is an enlarged sectional view of a part encircled by a solid line in FIG. 2 (*a*). FIG. 3 is a plan view of the injector piston nest 1 without a piston taken from a side of the open end 12, while FIG. 4 is a plan view of another piston nest 1 of this invention without a piston to be housed therein taken from a side of the open end 12 similarly as FIG. 3.

A piston nest 1 of this invention preferably comprises a general-purpose resin such as polypropylene. However, as a sterilizing treatment is sometimes done in a situation where pistons are housed in the piston nest, a material resistant to sterilization should be selected as the piston nest. For example, a material of high softening point (high melting point) for vapor sterilization and that of high radiation resistance for radiation sterilization should be selected.

The present piston nest 1 comprises a base material 2 and plural barrel-shaped, or cylindrical as shown in FIGS. 1 to 3, housing portions 3 for injector pistons, in which one surface of the base material 2 is opened as open ends 9 while the plural housing portions 3 are formed by piercing the base material 2 vertically thereto from the other open end 12, and protruding to the other side of the base material 2. The piston housing portions 3 and the base material 2 are integrally formed in FIG. 1, however, only barrel-shaped piston housing portions 3 may be prepared separately and then fitted into pierced plural holes which are also separately formed on the base material 2 at predetermined intervals.

The most characteristic structural feature of the piston nest 1 shown in FIG. 2 is that an expanded portion is formed as a thicker portion compared with surroundings on the peripheral surface toward inside or center axis side by expanding a part of a surrounding wall 6 of the piston housing portion, for example, an inner wall in the vicinity of an end portion thereof, i.e., a position near to an open end 9 apart from the center.

In general, an indent 10 is formed on an outer surface of a piston 5 in the peripheral direction to a longitudinally rear side from the center, i.e., at a plunger fitting side, so that the piston 5 to be housed in the piston housing portion 3 slides smoothly on an inner surface of an injection cylinder when the piston 5 is inserted into it. The expanded portion 4 slightly fits with the indent 10 formed in the vicinity of a rear end 8 of the piston 5, i.e., at the plunger fitting side, which functions as a fixing means the piston 5 housed therein and the piston nest 1.

Although an inner wall surface of the expanded portion 4 partially formed on the inner peripheral surface of the piston housing portion 3 is relatively wide and gentle, the expanded portion 4 may be a convex shape having a square or triangle cross section parallel to the axis. From a point of view to prevent development of peripheral flaws of the piston 5, it is more preferable to shape the inner wall surface into an expanded portion of relatively wide and inwardly gentle to the axis as shown in FIGS. 2 and 3.

The expanded portion 4 is formed singly or severally on the inner peripheral surface of the piston housing portion 3 not entirely but at a position thereon near to the open end 9 apart from the center. When the expanded portion 4 is single, it is formed in the shape of ring on the same inner peripheral surface of the cylindrical piston housing portion 3 as shown in FIGS. 2 and 3, while the expanded portion 4 may also be dotted on the same inner peripheral surface in the shape of bump as shown in FIG. 4 in which three dots are formed.

Preferably, an inner diameter (A) of the piston housing portion 3 is nearly uniform except the expanded portion 4, while an opened diameter of at least one of the open ends 9 and 12 where the piston 5 goes in and out is slightly larger than A, so that the piston 5 runs smoothly without developing flaws thereon.

According to this embodiment, the inner diameter of the piston 5 is nearly uniform as described above, but there may be structured to diminish the inner diameter from one open end to the other except the expanded portion 4. Due to such a inner diameter diminished structure of the piston housing portion 3, the pistons 5 go in and out easily through the open end of larger diameter and can be taken out all the pistons 5 housed therein at once by turning the piston nest inside over and turning the open end of larger diameter downward.

Further, in the injector piston nest in which the expanded portion 4 is formed on the inner wall surface of the piston housing portion 3, when the outer diameter (B) of the piston 5 to be housed except the indent 10, i.e., a maximum diameter thereof, is slightly smaller than the inner diameter (A) of the piston housing portion 3 except the expanded portion 4 (A>B) so as to leave at least partial clearance 11 between the inner peripheral surface of the piston housing portion 3 except the expanded portion 4 and the outer peripheral surface of the piston 5 under a condition where the piston 5 is housed in the piston housing portion 3, a vapor sterilizing treatment thereof can be conducted completely because vapor spreads sufficiently around the piston 5 under the above mentioned situation without developing flaws on the outer peripheral surface of the piston 5 when the piston 5 go in and out through the piston housing portion 3.

Figure 5:
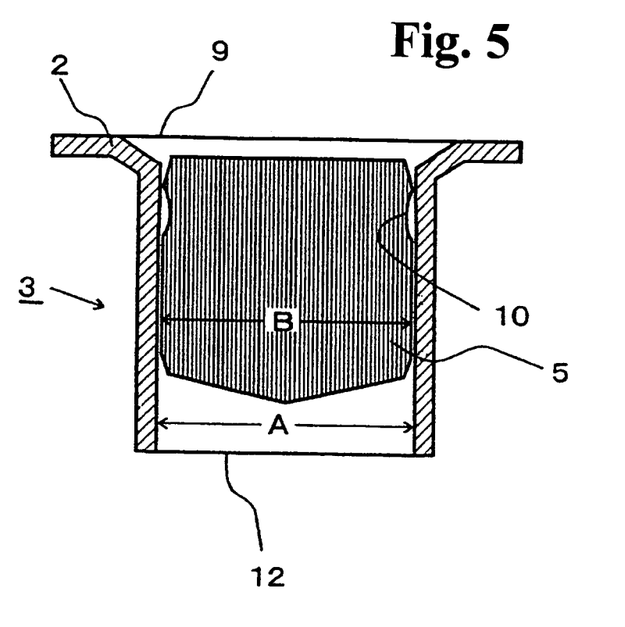
FIG. 5 is a sectional view of yet another injector piston nest of this invention with a piston housed therein taken from a parallel surface to the axis.

FIG. 5 is an enlarged sectional view of yet another injector piston nest of this invention with a piston housed in a piston housing portion. Symbols to designate specific portions in FIG. 5 are similarly used as FIGS. 1 to 4.

The present piston nest is the same as those nests described in FIGS. 1 to 4 except structure of the piston housing portion 3.

The piston housing portion 3 of the present piston nest is nearly cylindrical in shape having a circular section vertical to the axis and open ends on both sides, which is similar as that of described in FIG. 2 in this connection.

No expanded portion is formed on the inner wall surface of the piston housing portion 3 in the present piston nest, while the inner diameter (A) of one open end of the piston housing portion 3 is different from that (B) of the other end (A≠B), so as to form a structure in which the inner diameter of the piston housing portion 3 diminishes from one side of open end, e.g., the open end 12, to the other side, e.g., the open end 9.

When the piston 5 is housed in the piston housing portion of the present piston nest in which the inner diameter (A) of either one of the open ends of the piston housing portion 3 is smaller than the maximum outer diameter (B) of the piston 5, the outer wall of the piston 5 is pressed inward in the direction of center axis by the inner wall surface of the piston housing portion 3 to fix it in the piston housing portion 3 by resisting such pressing force, thereby preventing the piston from dropping out.

Figure 6:
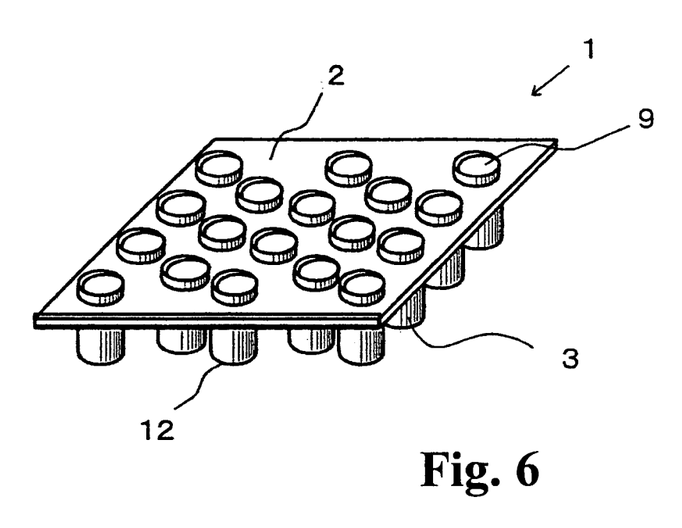
FIG. 6 is a perspective view of still another injector piston nest of this invention.

FIG. 6 is a perspective view of still another injector piston nest of this invention. Piston nests shown in FIGS. 1 to 5 have a structure in which one of the open end 9 or 12 of the piston housing portion 3 is located on the same surface as one of surfaces of a base material 2 and the other open end is protruded to the opposite side. On the other hand, according to the present piston nest, both open ends 9 and 12 of the piston housing portion 3 are protruded from both surfaces of the base material 2 as shown in FIG. 6. Although the locational relationship between the base material 2 and the piston housing portion 3 is peculiar to the present piston nest as described above, other features such as an inner structure of the piston housing portion 3 are not different from the rest embodiments of this invention described in FIGS. 1 to 5.

It should be understood that an entrance and an exit for the piston 5 to and from the piston housing portion 3 may either be the open end formed on the same side or respective different open end.

According to the present piston nest, a piston 5 of given shape and dimension and capable of being housed is inserted from either one of open ends formed on both sides of the piston housing portion 3 and housed therein by gently fitting the indent 10 of the piston 5 to the expanded portion 4 on the inner wall of the piston housing portion 3.

After the piston nest with pistons 5 housed therein is supplied to injector fabrication sites belonging to, for example, medical and pharmaceutical companies, pistons 5 are taken out of the present piston nest and assembled with other injector components into an injector.

Combination of the present piston nest with an injection cylinder nest makes such an injector fabrication process more effective. Conventionally, injection cylinders have been flowed one by one on a production line of pharmaceutical companies but, now, it is possible to handle them in the lump as each unit of nest according to the present invention.

More definitely, each injection cylinder capped with a nozzle cap is flowed to an injection liquid filling line to fill the liquid in the lump as a unit of nest. Production of pre-filled syringes as a unit nest can be done as in the following. At first, a location of the piston housing portion of the piston nest is adjusted on that of an injector housing portion of the injection cylinder housing portion and then the piston nest is located on that of the injection cylinder nest filled with the liquid followed by dropping down pistons housed in the housing portion into the injection cylinder in the lump.

It is not necessary to take out injection cylinders and pistons from respective nests according to the above mentioned method, which can be conducted quite hygienically without development of fine particles caused by going in and out thereof. In addition, production of pre-filled syringes can be done as a unit of several tens to several hundreds of components to be housed in a nest, which greatly improves the syringe production efficiency.

INDUSTRIAL EFFICACY

The injector piston nest of this invention is used successfully and conveniently for sterilizing, storing and transporting injector pistons without developing flaws on the surface of the piston.

What is claimed is:

1. A combination comprising injector pistons and a piston nest for housing the injector pistons, comprising:
   a flat base plate having a plurality of openings, and front and back sides,
   plural cylindrical housing portions having two open ends for receiving the injector pistons therein, said plural cylindrical housing portions protruding substantially perpendicularly from the back side of the base plate to surround the openings, and
   annular expanded portions, each being formed on an inner wall of each of said housing portions to protrude inwardly from an inner peripheral surface thereof,
   wherein the injector pistons are completely housed in said piston nest for housing the injector pistons,
   said injector piston has an indent on a part of an outer peripheral surface of the injector piston in a peripheral direction,
   a shape of the annular expanded portion fits with a shape of the indent,
   said indent engages said expanded portion of the housing portion so that said injector piston is kept in said housing portion,
   an inner diameter of each of said housing portions except for an inner diameter of said expanded portion is substantially uniform,
   each of said housing portions comprises two inner walls inside each of said housing portions having same inner diameters and extending upwardly and downwardly from two edges of each of the annular expanded portions, and clearance is at least partially formed between the outer peripheral surface of said injector piston and the inner peripheral surface except said expanded portion on said housing portion.

2. A combination as claimed in claim 1, wherein each of the annular expanded portions is formed annularly intermittently to be spaced apart from each other on the inner wall of each of said housing portions.

3. A combination as claimed in claim 1, wherein an opened diameter of at least one of open ends of each of the housing portions is slightly larger than the inner diameter of each of the housing portions so that the injection piston runs smoothly in each of the housing portions.

4. A combination as claimed in claim 3, wherein each of the injector pistons is inserted from the at least one of open ends of each of the housing portions having the opened diameter slightly larger than the inner diameter of each of the housing portions and dropped down from another open end other than the at least one of open ends.

5. A combination as claimed in claim 1, wherein
the injector piston has a cutout portion in the peripheral direction thereof on an end of the injector piston, and
a diameter of the end of the injector piston is smaller than a maximum diameter of the injector piston.

6. A combination as claimed in claim 1, wherein a maximum diameter of the injector piston is smaller than a minimum diameter of each of the housing portions except for a part where each of the expanded portions is present.

\* \* \* \* \*